United States Patent [19]
Andree et al.

[11] Patent Number: 5,300,676
[45] Date of Patent: Apr. 5, 1994

[54] HERBICIDAL FLUORINE-SUBSTITUTED ALPHA-(5-ARYLOXYNAPHTHALEN-1-YL-OXY)-PROPIONIC ACID DERIVATIVES

[75] Inventors: Roland Andree, Langenfeld; Michael Haug; Klaus Lürssen, both of Bergisch Gladbach; Hans-Joachim Santel, Leverkusen; Robert R. Schmidt, Bergisch Gladbach, all of Fed. Rep. of Germany

[73] Assignee: Bayer Aktiengesellschaft, Leverkusen, Fed. Rep. of Germany

[21] Appl. No.: 684,545

[22] Filed: Apr. 11, 1991

[30] Foreign Application Priority Data

Apr. 21, 1990 [DE] Fed. Rep. of Germany ....... 4012711

[51] Int. Cl.$^5$ ............................................. C07C 69/76
[52] U.S. Cl. ...................................... 560/56; 562/429; 562/466; 562/840; 564/150; 564/161; 564/172; 558/257; 544/243; 546/342; 556/437; 548/376.1; 549/76; 549/79; 549/501; 504/145
[58] Field of Search ................... 560/56; 502/429, 460, 502/840; 564/150, 161, 170; 558/257; 544/243; 540/342; 556/437; 548/378; 549/76, 79, 501; 504/145

[56] References Cited

FOREIGN PATENT DOCUMENTS 0308755 3/1989 European Pat. Off. .
0309864 4/1989 European Pat. Off. .
0347679 12/1989 European Pat. Off. .

OTHER PUBLICATIONS

Chemical Abstracts, vol. 107, No. 25, (Dec. 21, 1987), Columbus, Ohio, U.S.; Abstract No. 236243, p. 742, col. 1.

Primary Examiner—Paul J. Killos
Attorney, Agent, or Firm—Sprung Horn Kramer & Woods

[57] ABSTRACT

Fluorine-substituted α-(5-aryloxy-naphthalen-1-yl-oxy)-propionic derivatives of the formula

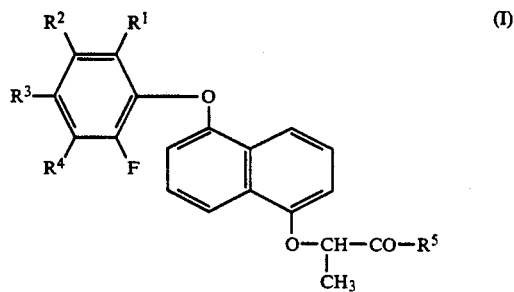

wherein $R^1$, $R^2$, $R^3$, $R^4$ and $R^5$, as defined herein, are useful as herbicides. Processes and intermediates for their preparation are also disclosed.

5 Claims, No Drawings

HERBICIDAL FLUORINE-SUBSTITUTED ALPHA-(5-ARYLOXYNAPHTHALEN-1-YL-OXY)-PROPIONIC ACID DERIVATIVES

The invention relates to new fluorine-substituted α-(5-aryloxy-naphthalen-1-yl-oxy)-propionic acid derivatives, to processes and to new intermediates for their preparation, and to their use as herbicides.

It is already known that certain α-(5-aryloxy-naphthalen-1-yl-oxy)-propionic acid derivatives such as, for example, ethyl α-(5-(4-trifluoromethyl-phenoxy)-naphthalen-1-yl-oxy)-propionate, are herbicidally active (cf. EP-A 309,864 corresponding to U.S. Ser. No. 07/247,817, filed Sep. 22, 1988, now allowed). However, the action of these known compounds against weeds and their tolerance by crop plants are not always entirely satisfactory.

New fluorine-substituted α-(5-aryloxy-naphthalen-1-yl-oxy)-propionic acid derivatives of the general formula (I)

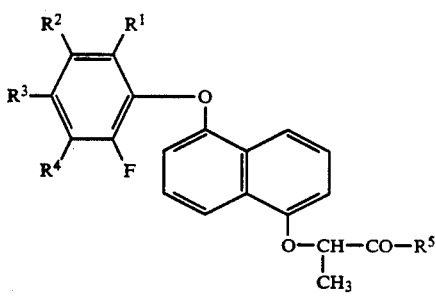

in which
- $R^1$ represents hydrogen, fluorine or cyano,
- $R^2$ represents hydrogen, fluorine or chlorine,
- $R^3$ represents fluorine, chlorine, cyano, trifluoromethyl or trifluoromethylsulphonyl,
- $R^4$ represents hydrogen, fluorine or chlorine and
- $R^5$ represents chlorine, hydroxyl, amino, $C_1$-$C_6$-alkylamino, $C_3$-$C_4$-alkenylamino, $C_3$-$C_4$-alkinylamino, phenylamino, benzylamino, $C_1$-$C_4$-alkoxycarbonyl-$C_1$-$C_2$-alkylamino, cyanoamino, di-($C_1$-$C_4$-alkyl)-amino, di-($C_3$-$C_4$-alkenyl)-amino, $C_1$-$C_4$-alkylsulphonylamino, phenylsulphonylamino, tolylsulphonylamino, hydroxylamino, $C_1$-$C_6$-alkoxyamino, N-($C_1$-$C_6$-alkoxy)-N-($C_1$-$C_4$-alkyl)-amino, hydrazino, $C_1$-$C_4$-alkylsulphonylhydrazino, phenylsulphonylhydrazino, tolylsulphonylhydrazino, $C_1$-$C_4$-alkylthio, phenylthio, benzylthio, $C_1$-$C_4$-alkoxy-carbonyl-$C_1$-$C_2$-alkylthio or the group —O—$R^6$ where represents a radical from the series comprising $C_1$-$C_6$-alkyl, $C_3$-$C_4$-alkenyl, $C_3$-$C_4$-alkinyl, $C_1$-$C_4$-alkoxy-$C_1$-$C_4$-alkyl, $C_1$-$C_4$-alkylthio-$C_1$-$C_4$-alkyl, $C_1$-$C_4$-alkylsulphinyl-$C_1$-$C_4$-alkyl, $C_1$-$C_4$-alkylsulphonyl-$C_1$-$C_4$-alkyl, phenoxy-$C_1$-$C_3$-alkyl, trimethylsilylmethyl, phenylthio-$C_1$-$C_3$-alkyl, benzyloxy-$C_1$-$C_3$-alkyl, benzylthio-$C_1$-$C_3$-alkyl, $C_1$-$C_4$-alkoxy-carbonyl-$C_1$-$C_2$-alkyl, $C_1$-$C_4$-alkylamino-carbonyl-$C_1$-$C_2$-allkyl, benzyl, pyrazolyl-$C_1$-$C_4$-alkyl, $C_2$-$C_4$-alkylideneaminooxy-$C_1$-$C_4$-alkyl and $C_2$-$C_4$-alkylideneamino, each of which is optionally substituted by fluorine and/or chlorine, or represents an ammonium, a $C_1$-$C_4$-alkylammonium, a sodium, potassium or calcium equivalent, or represents the group

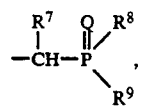

where
- $R^7$ represents hydrogen, $C_1$-$C_4$-alkyl, phenyl, furyl, thienyl or pyridyl,
- $R^8$ represents $C_1$-$C_4$-alkyl or $C_1$-$C_4$-alkoxy,
- $R^9$ represents $C_1$-$C_4$-alkoxy and
- Q represents oxygen or sulphur, or
- $R^6$ represents the group —$(CH_2)_n$—$R^{10}$ where
- n represents the numbers 0, 1, or 2 and
- $R^{10}$ represents a heterocyclic radical from the series comprising furyl, tetrahydrofuryl, oxotetrahydrofuryl, thienyl, tetrahydrothienyl, perhydropyranyl, oxazolyl, thiazolyl, thiadiazolyl, dioxolanyl, perhydropyrrolyl, oxoperhydropyrrolyl, isoxazolidinyl, pyridinyl or pyrimidinyl, each of which is optionally substituted by fluorine, chlorine, bromine and/or $C_1$-$C_4$-alkyl, have now been found.

The compounds of the formula (I) contain at least one asymmetrically substituted carbon atom and can therefore occur in various enantiomeric forms. The invention relates to the individual isomers which are possible and to mixtures of these isomers.

Furthermore, it has been found that the new fluorine-substituted α-(5-aryloxy-naphthalen-1-yl-oxy)-propionic acid derivatives of the formula (I) are obtained when (a) fluorine-substituted 5-aryloxy-1-naphthols of the general formula (II)

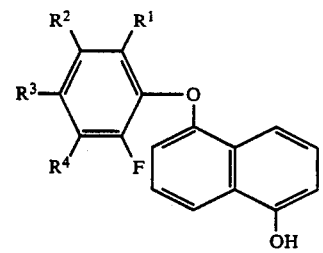

in which
$R^1$, $R^2$, $R^3$ and $R^4$ have the abovementioned meanings are reacted with propionic acid derivatives of the general formula (III)

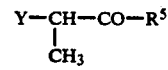

in which
- $R^5$ has been abovementioned meaning and
- Y represents a nucleophilic leaving group, if appropriate in the presence of an acid acceptor and if appropriate in the presence of a diluent, or (b) halogeno-benzene derivatives of the general formula (IV)

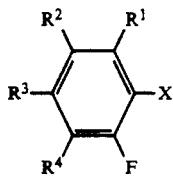

(IV)

in which
R¹, R², R³ and R⁴ have the abovementioned meanings and X represents halogen,
are reacted with α-(5-hydroxy-naphthalen-1-yl-oxy)-propionic acid derivatives of the general formula (V)

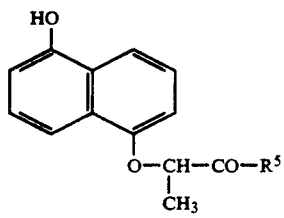

(V)

in which
R⁵ has the abovementioned meaning,
if appropriate in the presence of an acid acceptor and if appropriate in the presence of a diluent, or (c) in the event that R⁵ represents hydroxyl and the radicals R¹ to R⁴ have the abovementioned meanings, compounds of the general formula (I) in which R⁵ represents methoxy or ethoxy and the radicals R¹ to R⁴ have the abovementioned meanings, are reacted with alkali metal hydroxide in the presence of water and if appropriate in the presence of an organic solvent and the mixture is then acidified with a mineral acid, if appropriate after concentration, or (d) in the event that R⁵ represents chlorine and the radicals R¹ to R⁴ have the abovementioned meanings, compounds of the general formula (I) in which R⁵ represents hydroxyl and the radicals R¹ to R⁴ have the abovementioned meanings, are reacted with a chlorinating agent, if appropriate in the presence of a catalyst and if appropriate in the presence of a diluent, or (e) in the event that R⁵ has the abovementioned meaning, with the exception of chlorine, and the radicals R¹ to R⁴ have the abovementioned meanings, compounds of the general formula (I) in which R⁵ represents chlorine and the radicals R¹ to R⁴ have the abovementioned meanings, are reacted with compounds of the general formula (VI)

H—R⁵ (VI)

in which
R⁵ has the abovementioned meaning with the exception of chlorine,
if appropriate in the presence of an acid acceptor and if appropriate in the presence of a diluent, or (f) in the event that R⁵ represents the group —O—R⁶ where R⁶ has the abovementioned meaning with the exception of ammonium, alkylammonium, alkali metal and alkaline earth metal, and the radicals R¹ to R⁴ have the abovementioned meanings, compounds of the general formula (I) in which R⁵ represents hydroxyl and the radicals R¹ to R⁴ have the abovementioned meanings, are reacted with hydroxyl compounds of the general formula (VII)

HO—R⁶ (VII)

in which
R⁶ has the abovementioned meanings with the exception of ammonium, alkylammonium, alkali metal and alkaline earth metal,
if appropriate in the presence of a catalyst and if appropriate in the presence of a diluent.

Finally, it has been found that the new fluorine-substituted α-(5-aryloxy-naphthalen-1-yl-oxy)-propionic acid derivatives of the general formula (I) have excellent herbicidal properties.

Surprisingly, the fluorine-substituted α-(5-aryloxy-naphthalen-1-yl-oxy)-propionic acid derivatives of the formula (I) according to the invention have a considerably more powerful action than ethyl α-(5-(4-trifluoromethylphenoxy)-naphthalen-1-yl-oxy)-propionate, which is a previously known active substance of a similar structure and the same direction of action, while being well tolerated by crop plants.

The invention preferably relates to compounds of the formula (I) in which
R¹ represents hydrogen or fluorine,
R² represents hydrogen or fluorine,
R³ represents trifluoromethyl or trifluoromethylsulphonyl,
R⁴ represents hydrogen or fluorine, and
R⁵ represents chlorine, hydroxyl, amino, C₁-C₄-alkylamino, phenylamino, C₁-C₄-alkoxy-carbonyl-C₁-C₂-alkylamino, di-(C₁-C₃-alkyl)-amino, C₁-C₄-alkylsulphonylamino, phenylsulphonylamino, hydroxyamino, cyanoamino, C₁-C₄-alkoxyamino, N-(C₁-C₄-alkoxy)-N-(C₁-C₃-alkyl)-amino, hydrazino, C₁-C₄-alkylsulphonylhydrazino, phenylsulphonylhydrazino, C₁-C₄-alkylthio or C₁-C₄-alkoxy-carbonyl-C₁-C₂-alkylthio, or represents the group —O—R⁶ where R⁶ represents C₁-C₄-alkyl, C₁-C₂-alkoxy-C₁-C₂-alkyl, C₁-C₂-alkyl, C₁-C₂-alkylsulphonyl-C₁-C₂-alkyl, benzyloxy-C₁-C₃-alkyl, benzylthio-C₁-C₃-alkyl, C₁-C₄-alkoxycarbonyl-C₁-C₂-alkyl, C₁-C₁-C₄-alkylamino-carbonyl-C₁-C₂ -alkyl, benzyl, trimethylsilylmethyl, C₂-C₄-alkylidene-aminooxy-C₂-C₃-alkyl or represents an ammonium, C₁-C₃-alkyl-ammonium, sodium, or potassium equivalent, or represents the group

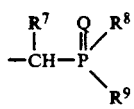

where
R⁷ represents hydrogen, methyl, phenyl, furyl, thienyl or pyridyl,
R⁸ represents methoxy or ethoxy,
R⁹ represents methoxy or ethoxy,
Q represents oxygen or sulphur,
or
R⁶ represents the group (—CH₂—)ₙ—R¹⁰ where
n represents the numbers 0, 1 or 2 and
R¹⁰ represents a heterocyclic radical from the series comprising furyl, tetrahydrofuryl, thienyl, perhydropyranyl, oxazolyl, thiazolyl, isoxazolidinyl and dioxolanyl, each of which is optionally substituted by chlorine and/or methyl.

In particular, the invention relates to compounds of the formula (I) in which $R^1$, $R^2$ and $R^4$ represent hydrogen, $R^3$ represents trifluoromethyl and $R^5$ represents chlorine, hydroxyl, methoxy, ethoxy, propoxy, isopropoxy, n-butoxy, isobutoxy, sec-butoxy, t-butoxy, methoxyethoxy, ethoxyethoxy, benzyloxyethoxy, benzyloxypropoxy, methoxycarbonylmethoxy, ethoxycarbonylmethoxy, methoxycarbonylethoxy, ethoxycarbonylethoxy or isopropylideneaminooxyethoxy.

The R isomers of the particularly preferred compounds of the formula (I) are very particularly preferred.

If, for example, 5-(2-fluoro-4-trifluoromethylphenoxy)-1-naphthol and ethyl α-bromo-propionate are used as starting substances for process (a) according to the invention, the course of the reaction can be represented by the following equation:

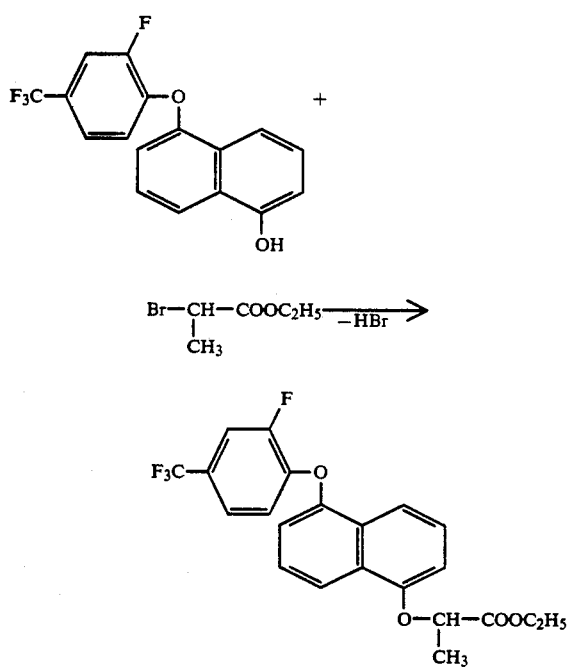

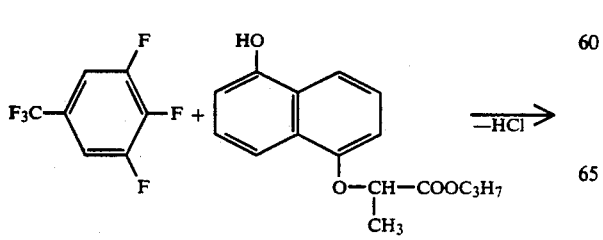

If, for example, 3,4,5-trifluoro-benzotrifluoride and propyl α-(5-hydroxy-naphthalen-1-yl-oxy)-propionate are used as starting substances for process (b) according to the invention, the course of the reaction can be represented by the following equation:

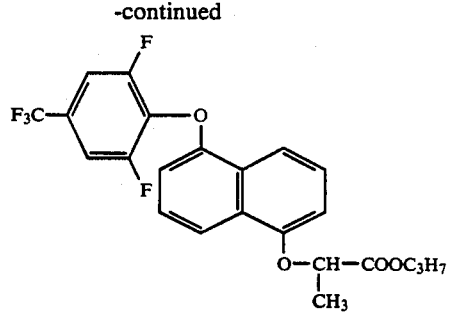

If, for example, methyl α-(5-(2-fluoro-4-trifluoromethyl-phenoxy)-naphthalen-1-yl-oxy)-propionate and sodium hydroxide solution are used as starting substances for process (c) according to the invention, the course of the reaction can be represented by the following equation:

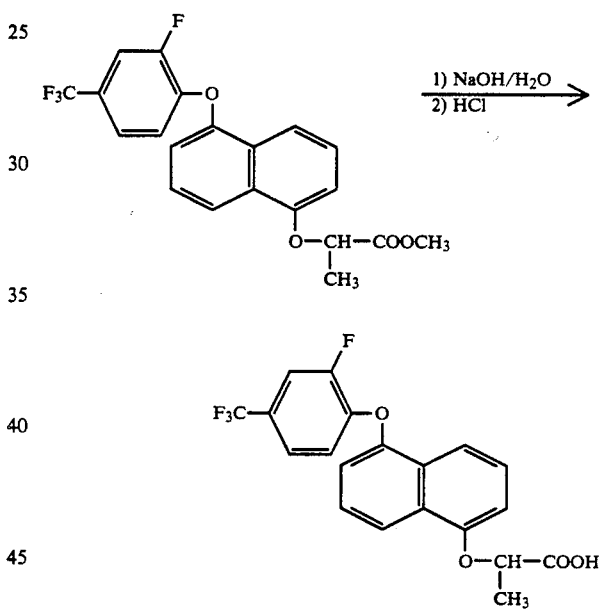

If, for example, α-(5-(2,3,6-trifluoro-4-trifluoromethylphenoxy)-naphthalen-1-yl-oxy)-propionic acid and thionyl chloride are used as starting substances for process (d) according to the invention, the course of the reaction can be represented by the following equation:

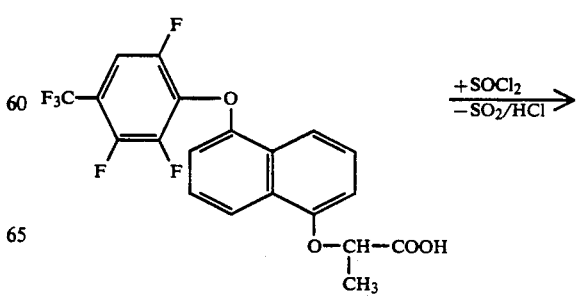

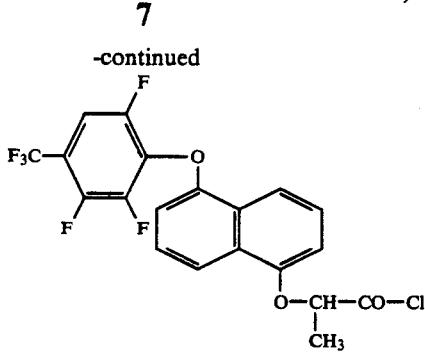

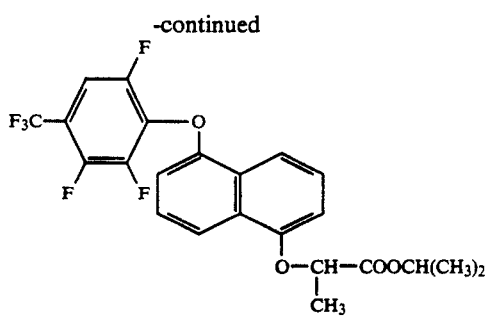

If, for example, α-(5-(2,6-difluoro-4-trifluoromethyl-phenoxy)-naphthanlen-1-yl-oxy)-propionyl chloride and butanol are used as starting substances for process (e) according to the invention, the course of the reaction can be represented by the following equation:

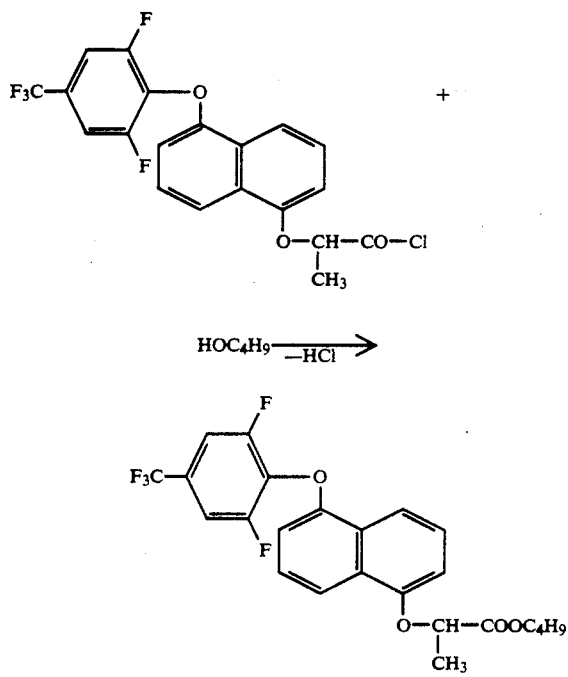

If, for example, α-(5-(2,3,6-trifluoro-4-trifluoromethylphenoxy)-naphthalen-1-yl-oxy)-propionic acid and isopropanol are used as starting substances for process (f) according to the invention, the course of the reaction can be represented by the following equation:

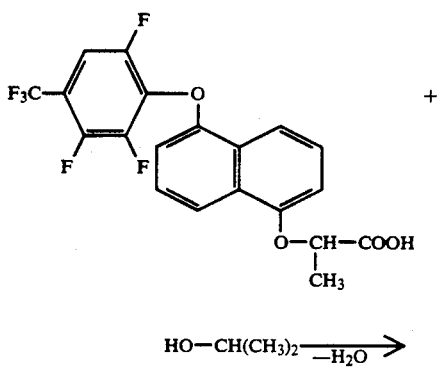

Formula (II) provides a general definition of the 5-aryloxy-1-naphthols to be used as starting substances in process (a) according to the invention for the preparation of compounds of the formula (I).

In formula (II), $R^1$, $R^2$, $R^3$ and $R^4$ preferably, or in particular, have those meanings which have already been mentioned above in connection with the description of the compounds of the formula (I) according to the invention as being preferred, or particularly preferred, for $R^1$, $R^2$, $R^3$ and $R^4$.

Examples of the starting substances of the formula (II) which may be mentioned are: 5-(2-fluoro-4-trifluoromethyl-phenoxy)-1-naphthol, 5-(2,6-difluoro-4-trifluoromethyl-phenoxy)-1 naphthol, 5-(2-cyano-6-fluoro-4-trifluoromethyl-phenoxy-1-naphthol, and 5-(2,3,6-trifluoro-4-trifluoromethyl-phenoxy)-1-naphthol.

The starting substances of the formula (II) were hitherto not known from the literature. The compounds of the formula (II) are obtained when corresponding halogeno-benzene derivatives of the general formula (IV)

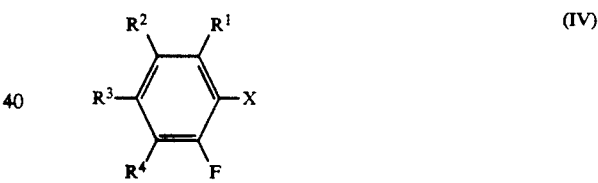

in which
$R^1$, $R^2$, $R^3$, $R^4$ and X have the abovementioned meanings, are reacted with 1,5-dihydroxynaphthalene in the presence of an acid acceptor such as, for example, sodium hydroxide or potassium hydroxide, and in the presence of a diluent such as, for example, dimethylformamide, dimethylacetamide, dimethyl sulphoxide, tetramethylene sulphone or N-methyl-pyrrolidone, at temperatures between 20° C. and 150° C., and the product is worked up by customary methods.

Formula (IV) provides a general definition of the halogeno-benzene derivatives. In formula (IV), $R^1$, $R^2$, $R^3$ and $R^4$ preferably, or in particular, have those meanings which have already been mentioned in connection with the description of the compounds of the formula (I) according to the invention as being preferred, or particularly preferred, for $R^1$, $R^2$, $R^3$ and $R^4$, and X preferably represents chlorine or fluorine.

Examples of the halogenobenzene derivatives of the formula (IV) which may be mentioned are: 3,4-difluoro-benzotrifluoride, 3,4,5-trifluoro-benzotrifluoride, 2,3,4,5-tetrafluoro-benzotrifluoride and 3-cyano-4,5-difluoro-benzotrifluoride.

The compounds of the formula (IV) are known and/or can be prepared by processes known per se (cf. J. Chem. Soc. 1969, 211–217; ibid. 1971, 1547–1549; EP-A 34,402; U.S. Pat. No. 4,424,396; EP-A 145,314; U.S. Pat. No. 4,808,750; FR-A 2,538,380 (Chem. Abstracts 102 (1985), 61914x)).

Formula (III) provides a general definition of the propionic acid derivatives furthermore to be used as starting substances in process (a) according to the invention. In formula (III), $R^5$ preferably, or in particular, has the meaning which has already been mentioned above in connection with the description of the compounds of the formula (I) according to the invention as being preferred, or particularly preferred, and Y preferably represents chlorine, bromine, iodine, or $C_1$-$C_4$-alkylsulphonyloxy which is optionally substituted by fluorine or chlorine, or phenylsulphonyloxy which is optionally substituted by fluorine, chlorine, bromine or methyl, in particular represents chlorine, bromine, methylsulphonyloxy, phenylsulphonyloxy or 4-methylphenylsulphonyloxy.

Examples of the compounds of the formula (III) which may be mentioned are: the methyl, ethyl, propyl, isopropyl, butyl, isobutyl and sec-butyl esters of α-chloro-, α-bromo- and α-iodopropionic acid, and the methyl, ethyl, propyl, butyl, isopropyl, isobutyl and sec-butyl esters of α-methylsulphonyloxy-, α-ethylsulphonyloxy-, α-propylsulphonyloxy—, α-butylsulphonyloxy-, α-trifluoromethylsulphonyloxy-, α-phenylsulphonyloxy-and α-(4-methyl-phenylsulphonyloxy)-propionic acid.

The abovementioned compounds of the formula (III) are in each case understood as meaning the R isomers, the S isomers and the racemic mixtures of these isomers.

The starting substances of the formula (III) are known and/or can be prepared by processes known per se (cf. DE-OS (German Published Specification) 2,758,002, DE-OS (German Published Specification) 2,854,542).

Process (a) according to the invention for the preparation of the new compounds of the formula (I) is preferably carried out using diluents. Diluents which are suitable for this purpose are virtually all inert organic solvents. These preferably include aliphatic and aromatic, optionally halogenated hydrocarbons such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, ethers such as diethyl ether, dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methyl-pyrrolidone, and also dimethyl sulphoxide, tetramethylene sulphone and hexamethylphosphoric triamide.

Acid acceptors which can be employed in process (a) according to the invention are all acid-binding agents which can customarily be employed for reactions of this type. The following are preferably suitable: alkali metal hydroxides such as, for example, sodium hydroxide and potassium hydroxide, alkaline earth metal hydroxides such as, for example, calcium hydroxide, alkali metal carbonates and alkali metal alcoholates such as sodium carbonate, potassium carbonate, sodium tert-butylate and potassium tert-butylate, furthermore aliphatic, aromatic or heterocyclic amines, for example triethylamine, trimethylamine, dimethylaniline, dimethylbenzylamine, pyridine, 1,5-diazabicyclo-[4.3.0]-non-5-ene (DBN), 1,8 diazabicyclo-[5.4.0]-undec-7ene (DBU) and 1,4-diazabicyclo-[2.2.2]-octane (DABCO).

When carrying out process (a) according to the invention, the reaction temperatures can be varied within a substantial range. In general, the process is carried out at temperature between 0° C. and 150° C., preferably at temperatures between 20° C. and 100° C.

Process (a) according to the invention is generally carried out under atmospheric pressure. However, it is also possible to carry out the process under increased or reduced pressure.

For carrying out process (a) according to the invention, the starting substances required in each case are generally employed in approximately equimolar amounts. However, it is also possible to use one of the two components employed in each case in a larger excess. In general, the reactions are carried out in a suibable diluent in the presence of an acid acceptor, and the reaction mixture is stirred for several hours at the particular temperature required. Working-up in process (a) according to the invention is carried out in each case by customary methods (cf. the Preparation Examples).

The halogeno-benzene derivatives of the formula (IV) to be used as starting substances in process (b) according to the invention have already been described above.

Formula (V) provides a general definition of the α-(5-hydroxy-naphthalen-1-yl-oxy)-propionic acid derivatives furthermore to be used as starting substances in process (b) according to the invention. In formula (V), $R^5$ preferably, or in particular, has the meaning which has already been mentioned above in connection with the description of the compounds of the formula (I) according to the invention as being preferred or particularly preferred.

Examples of the starting substances of the formula (V) which may be mentioned are: the methyl, ethyl, propyl, isopropyl, butyl, isobutyl and sec-butyl esters of α-(5-hydroxy-naphthalen-1-yl-oxy)-propionic acid.

The starting substances of the formula (V) are known and/or can be prepared by processes known per se (cf. JP 79/32477, cited in Chem. Abstracts 91 (1979), 91510j).

Process (b) is preferably carried out using a diluent. Diluents which are suitable are, above all, those diluents which have already been mentioned in the description of process (a) according to the invention. Particularly preferred diluents are aprotic polar organic solvents such as, for example, acetone, acetonitrile, methyl ethyl ketone, propionitrile, diethylformamide, dimethylacetamide, dimethyl sulphoxide, sulpholane and N-methylpyrrolidone.

Process (b) is preferably carried out in the presence of an acid acceptor. Acid acceptors which are suitable are, above all, those which have already been mentioned in the description of process (a) according to the invention.

When carrying out process (b) according to the invention, the reaction temperatures can be varied within a substantial range. In general, the process is carried out at temperatures between 0° C. and 200° C., preferably at temperatures between 20° C. and 150° C.

In general, process (b), according to the invention is carried out under atmospheric pressure. However, it is also possible to carry out the process under increased or reduced pressure.

For carrying out process (b) according to the invention, between 0.5 and 2 moles, preferably between 0.7 and 1.5 moles, of α-(5-hydroxy-naphthalen-1-yl-oxy)-propionic acid derivative of the formula (V) are generally employed per mole of halogeno-benzene derivative of the formula (IV).

The reaction and working-up can be carried out as described above for process (a).

With the proviso that $R^5$ represents methoxy or ethoxy, formula (I) provides a general definition of the compounds to be used as starting substances in process (c) according to the invention. In this case, the radicals $R^1$, $R^2$, $R^3$ and $R^4$ preferably, or in particular, have those meanings which have already been mentioned above in connection with the description of the compounds of the formula (I) according to the invention as being preferred, or particularly preferred.

Examples of the starting substances for process (c) which may be mentioned are: the methyl and ethyl esters of α-(5-(2-fluoro-4-trifluoromethyl-phenoxy)-, α-(5-(2,6-difluoro-4-trifluoromethyl-phenoxy)-and α-(5-(2,3,6-trifluoro-4-trifluoromethyl-phenoxy)-naphthalen-1-yl-oxy)-propionic acid.

The above-described starting substances of the formula (I) for process (c) are new compounds according to the invention; they can be prepared by process (a) or (b) according to the invention.

Process (c) is carried out using alkali metal hydroxides. Examples for these which may be mentioned are lithium hydroxide, sodium hydroxide and potassium hydroxide. Sodium hydroxide is preferably used.

Process (c) is carried out in the presence of water and, if appropriate, in the presence of an organic solvent. Preferred organic solvents which are employed are alcohols such as, for example, methanol or ethanol.

For the acidification in process (c), the customary mineral acids such as, for example, hydrochloric acid or sulphuric acid, are used.

When carrying out process (c) according to the invention, the reaction temperatures can be varied within a substantial range. In general, the process is carried out at temperatures between 10° C. and 150° C., preferably at temperatures between 20° C. and 100° C.

Process (c) according to the invention is generally carried out under atmospheric pressure. However, it is also possible to carry out the process under increased or reduced pressure.

For carrying out process (c), between 0.1 and 10 moles, preferably between 0.5 and 2 moles, of alkali metal hydroxide are generally employed per mole of starting compound of the formula (I). In general, the reactants are combined at room temperature, and the reaction mixture is stirred until the reaction is complete, if appropriate at an increased temperature. If appropriate, the mixture is concentrated, cooled and acidified, and the reaction product which is obtained in crystalline form can be isolated by filtration with suction.

With the proviso that $R^5$ represents hydroxyl, formula (I) provides a general definition of the compounds to be used as starting substances in process (d) according to the invention. In this case, the radicals $R^1$, $R^2$, $R^3$ and $R^4$ preferably, or in particular, have those meanings which have already been mentioned above in connection with the description of the compounds of the formula (I) according to the invention, as being preferred, or particularly preferred.

Examples of the starting substances for process (d) which may be mentioned are: α-(5-(2-fluoro-4-trifluoromethyl-phenoxy)-, α-(5-(2,6-difluoro-4-trifluoromethyl-phenoxy)-and α-(5-(2,3,6-trifluoro-4-trifluoromethyl-phenoxy)-naphthalen-1-yl-oxy)-propionic acid.

The above-described starting substances of the formula (I) for process (d) are new compounds according to the invention; they can be prepared by process (c) according to the invention.

Process (d) is carried out using a chlorinating agent. Chlorinating agents which can be employed are the customary agents for the reaction of carboxylic acids to carboxylic acid chlorides. Examples which may be mentioned of these are phosgene, thionyl chloride, phosphoryl chloride and benzotrichloride. Thionyl chloride is preferably used as the chlorinating agent.

If appropriate, process (d) is carried out in the presence of a catalyst. Catalysts which can be used are those which are customary for the preparation of acid chlorides from acids such as, for example, pyridine or dimethylformamide.

If appropriate, process (d) is carried out in the presence of a diluent. Preferred diluents which are suitable are inert organic solvents from the series of the halogenated hydrocarbons such as, for example, methylene chloride, chloroform, tetrachloromethane or 1,2-dichloroethane.

When carrying out process (d) according to the invention, the reaction temperatures can be varied within a substantial range. In general, the process is carried out at temperatures between 0° C. and 100° C., preferably at temperatures between 10° C. and 90° C.

Process (d) is generally carried out under atmospheric pressure.

For carrying out process (d), between 1 and 100 moles, preferably between 2 and 50 moles, of chlorinating agent are generally employed per mole of starting compound of the formula (I). In general, the reactants are combined at room temperature, and the reaction is stirred until the reaction is complete, if appropriate at an increased temperature. The reaction product which remains after the volatile components have been distilled off under reduced pressure can be purified by recrystallization, but can also be employed for subsequent reactions without further purification.

With the proviso that $R^5$ represents chlorine, formula (I) provides a general definition of the compounds to be used as starting substances in process (e) according to the invention. In this case, the radicals $R^1$, $R^2$, $R^3$ and $R^4$ preferably, or in particular, have those meanings which have already been mentioned above in connection with the description of the compounds of the formula (I) according to the invention as being preferred, or particularly preferred.

Examples of the starting substances for process (e) which may be mentioned are: α-(5-(2-fluoro-4-trifluoromethyl-phenoxy)-, α-(5-(2,6-difluoro-4-trifluoromethyl-phenoxy)-and α-(5-(2,3,6-trifluoro-4-trifluoromethyl-phenoxy)-naphthalen-1-yl-oxy)-propionyl chloride.

The above-described starting substances of the formula (I) for process (e) are new compounds according to the invention; they can be prepared by process (d) according to the invention.

Formula (VI) provides a general definition of the compounds furthermore to be employed as starting substances in process (e) according to the invention. In formula (VI), $R^5$ preferably, or in particular, has the meaning which has already been mentioned above in connection with the description of the compounds of the formula (I) according to the invention as being preferred, or particularly preferred.

Examples of the starting substances of the formula (VI) which may be mentioned are: methylamine, ethylamine, propylamine, isopropylamine, aniline, cyanoamide, dimethylamine, diethylamine, hydroxylamine, O-methylhydroxylamine, hydrazine, methylsulphonylhydrazine, methanol, ethanol, propanol, isopropanol, butanol, isobutanol, sec-butanol, 2-methoxyethanol, 2-ethoxy-ethanol, 2-methylthio-ethanol, 2-ethylthio-ethanol, 2-benzyloxy-ethanol, 3-benzyloxypropanol, 2-benzylthio-ethanol, diethyl and dimethyl hydroxymethanephosphonate, dimethyl and diethyl 1-hydroxy-ethane-phosphonate, dimethyl and diethyl 1-hydroxy-1-phenyl-methanephosphonate, acetone oxime, 3-hydroxyfuran, furfuryl alcohol, perhydrofurfuryl alcohol, methyl lactate, ethyl lactate, methyl glycolate and ethyl glycolate.

These compounds are known chemicals for synthesis.

Process (e) is preferably carried out using a diluent. Diluents which are suitable are, above all, those which have already been mentioned in the description of process (a) according to the invention.

Process (e) is preferably carried out in the presence of an acid acceptor. Acid acceptors which are suitable are, above all, those which have already been mentioned in the description of process (a) according to the invention.

When carrying out process (e) according to the invention, the reaction temperatures can be varied within a substantial range. In general, the process is carried out at temperatures between $-20°$ C. and $+100°$ C, preferably at temperatures between $0°$ C. and $50°$ C.

Process (e) according to the invention is generally carried out under atmospheric pressure. However, it is also possible to carry out the process under increased or reduced pressure.

For carrying out process (e) according to the invention, the starting substances required in each case are generally employed in approximately equimolar amounts. However, it is also possible to use one of the two components employed in each case in a larger excess. In general, the reactions are carried out in a suitable diluent in the presence of an acid acceptor, and the reaction mixture is stirred for several hours at the particular temperature required.

Working-up in process (e) according to the invention is carried out in each case by customary methods (cf. the Preparation Examples).

With the proviso that $R^5$ represents hydroxyl, formula (I) provides a general definition of the compounds to be used as starting substances in process (f) according to the invention. In this case, the radicals $R^1$, $R^2$, $R^3$ and $R^4$ preferably, or in particular, have those meanings which have already been mentioned above in connection with the description of the compounds of the formula (I) according to the invention as being preferred, or particularly preferred.

Examples of the starting substances of the formula (I) for process (f) which may be mentioned are: α-(5-(2-fluoro-4-trifluoromethyl-phenoxy)-, α-(5-(2,6-difluoro-4-trifluoromethyl-phenoxy)-and α-(5-(2,3,6-trifluoro-4-trifluoromethyl-phenoxy)-naphthalen-1-yloxy)-propionic acid.

The above-described starting substances of the formula (I) for process (f) are new compounds according to the invention; they can be prepared by process (c) according to the invention.

Formula (VII) provides a general definition of the compounds furthermore to be employed as starting substances in process (f) according to the invention. In formula (VII), $R^6$ preferably represents $C_1-C_6$-alkyl, $C_3-C_4$-alkenyl, $C_3-C_4$-alkinyl, $C_1-C_4$-alkoxy-$C_1-C_4$-alkyl, $C_1-C_4$-alkylthio-$C_1-C_4$-alkyl, phenoxy-$C_1-C_3$-alkyl, trimethylsilylmethyl, phenylthio-$C_1-C_3$-alkyl, benzyloxy-$C_1-C_3$-alkyl, benzylthio-$C_1-C_3$-alkyl or $C_1-C_4$-alkoxy-carbonyl-$C_1-C_2$-alkyl.

The starting substances of the formula (VII) are known chemicals for synthesis.

Process (f) is preferably carried out using a diluent. Diluents which are suitable are, in particular, the hydroxy compounds of the formula (VII) which are employed as reactants in process (f).

Process (f) is preferably carried out in the presence of a catalyst. Preferred catalysts which are suitable are strong acids such as, for example, sulphuric acid, hydrochloric acid, p-toluenesulphonic acid and methanesulphonic acid.

When carrying out process (f) according to the invention, the reaction temperatures can be varied within a substantial range. In general, the process is carried out at temperatures between $0°$ C. and $150°$ C., preferably at temperatures between $20°$ C. and $100°$ C.

In general, process (f) according to the invention is carried out under atmospheric pressure. However, it is also possible to carry ut the process under increased or reduced pressure.

For carrying out process (f), the starting compound of the formula (VII) is generally employed in excess so that it also acts as a diluent.

The reaction and working-up can be carried out by customary methods (cf. the Preparation Examples).

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the commands can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land, and for the selective combating of weeds in annual cultures.

In particular, the compounds of the formula (I) according to the invention are suitable for selectively combating, above all, monocotyledon weeds in monocotyledon and dicotyledon crops, both in pre-emergence and post-emergence processes.

To a certain extent, the compounds of the formula (I) also have an insecticidal action.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example ligninsulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H, 3H)-dione (AMETHYDIONE) or N-(2-benzothiazolyl)-N,N'-dimethylurea (METABENZTHIAZURON) for combating weeds in cereals; 4-amino-3-methyl-6-phenyl-1,2,4-triazin-5(4H)-one (METAMITRON) for combating weeds in sugar beet and 4-amino-6-(1,1-dimethylethyl)-3-methylthio-1,2,4-triazin-5 (4H)-one (METRIBUZIN) for combating weeds in soya beams, furthermore also 2,4-dichlorophenoxyacetic acid (2,4-D); 4-(2,4-dichlorophenoxy)-butric acid (2,4-DB); 2,4-dichlorophenoxypropionic acid (2,4-DP); 5-(2-chloro-4-trifluoromethyl-phenoxy)-2-nitro-benzoic acid (ACIFLUORFEN); 2-chloro-2',6'-diethyl-N-(methoxymethyl)acetanilide (ALACHLOR); 4-amino-benzenesulphonyl-methylcarbonate (ASULAM); 2-chloro-4-ethylamino-6-isopropylamino-1,3,5-triazine (ATRAZINE); methyl 2-[[[[[(4,6-dimethoxypyrimidin-2-yl)-amino]-carbonyl]-amino]-sulphonyl]-methyl]-benzoate (BENSULFURON); 3-isopropyl-2,1,3-benzothiadiazin-4-one-2,2-dioxide (BENTAZONE); methyl 5-(2,4-dichlorophenoxy)-2-nitrobenzoate (BIFENOX); 3,5-dibromo-4-hydroxy-benzonitril; (BROMOXYNIL); N-(butoxymethyl)-2-chloro-N-(2,6-diethylphenyl)-acetamide (BUTACHLOR); 5-amino-4-chloro-2-phenyl-2,3-dihydro-3-oxypyridazine (CHLORIDAZON); ethyl 2-{[(4-chloro-6-methoxy-2-pyrimidinyl)-aminocarbonyl]-aminosulphonyl}-benzoate (CHLORIMURON); N-(3-chlorophenyl)-isopropylcarbamate (CHLORPROPHAM); 2-chloro-N-{[(4-methoxy-6-methyl-1,3,5-triazin-2-yl)-amino]-carbonyl}-benzenesulphonamide (CHLORSULFURON); N,N-dimethyl-N'-(3-chloro-4-methylphenyl)-urea (CHLORTOLURON); exo-1-methyl-4-(1-methylethyl)-2-(2-methylphenyl-methoxy)-7-oxabicyclo-(2,2,1) -heptane (CINMETHYLIN); 3,6-dichloro-2-pyridinecarboxylic acid (CLOPYRALID); 2-chloro-4-ethylamino-6-(3-cyanopropylamino)-1,3,5-triazine (CYANAZINE); N,S-diethyl-N-cyclohexylthiocarbamate (CYCLOATE); 2-[4-(2,4-dichlorophenoxy)phenoxy]-propionic acid, its methyl ester or its ethyl ester (DICLOFOP); 2-[(2-chlorophenyl)-methyl]-4,4-dimethylisoxazolidin-3-one (DIMETHAZONE); S-ethyl N,N-di-n-propylthiocarbamidate (EPTAME); 4-amino-6-t-butyl-3-ethylthio-1,2,4-triazin-5(4H)-one (ETHIOZIN); N,N-di-methyl-N'-(3-trifluoromethylphenyl)-urea (FLUOMETURON); 1-methyl-3-phenyl-5-(3-trifluoromethylphenyl)-4-pyridone (FLURIDONE); [(4-amino-3,5-dichloro-6-fluoro-2-pyridinyl)-oxy]-acetic acid or its 1-methylheptyl ester (FLUROXYPYR); 5-(2-chloro-4-trifluoromethylphenoxy)-N-methylsulphonyl-2-nitrobenzamide (FOMESAFEN); 3-cyclohexyl-6-dimethylamino-1-methyl-1,3,5-triazine-2,4-dione (HEXAZINONE); methyl 2-[4,5-dihydro-4-methyl-4-(1-methylbenzoate (IMAZAMETHABENZ); 2-[5-methyl-5-(1-methylethyl)-4-oxo-2-imidazolin-2-yl]-3-quinolincarboxylic acid (IMAZAQUIN); 2-[4,5-dihydro-4-methyl-4-isopropyl-5-oxo(1H)-imidazol-2-yl]-5-ethylpyridin -3-carboxylic acid (IMAZETHAPYR); 3,5-diiodo-4-hydroxybenzonitrile (IOXYNIL); N,N-dimethyl-N'-(4-isopropylphenyl)-urea (ISOPROTURON); 2-ethoxy-1-methyl-2-oxoethyl 2-[2-chloro-4-(trifluoromethyl)-phenoxy]-2-nitrobenzoate (LACTOFEN); (2-methyl-4-chlorophenoxy)-acetic acid (MCPA); (4-chloro-2-methylphenoxy)-propionic acid (MCPP); N-methyl-2-(1,3-benzothiazol-2-yloxy)-acetanilide (MEFENACET); 2-chloro-N-(2,6-dimethylphenyl)-N-[(1H)-pyrazol-1-yl-methyl]acetamide (METAZACHLOR); 2-ethyl-6-methyl-N-(1-methyl-2-methoxyethyl)-chloroacetanilide (METOLACHLOR); 2-{[[((4-methoxy-6-methyl-1,3,5-triazin-2-yl)-amino)-carbonyl]amino]-sulphonyl}-benzoic acid or its methyl ester (METSULFURON); S-ethyl N,N-hexamethylenethiocarbamate (MOLINATE); 4-(di-n-propylamino)-3,5-dinitrobenzenesulphonamide (ORYAZLIN); 2-chloro-4-trifluoromethylphenyl 3-ethoxy-4-nitro-phenyl ether (OXYFLUORFEN); N-(1-ethylpropyl)-3,4-dimethyl-2,6-dinitroaniline (PENDIMETHALIN); 3-(ethoxycarbonylaminophenyl) N-(3'-methylphenyl)-carbamate (PHENMEDIPHAM); 2-chloro-N-isopropylacetanilide (PROPACHLOR); isopropyl N-phenyl-carbamate (PROPHAM); O-(6-chloro-3-phenyl-pyridazin-4-yl) S-octyl thiocarbonate (PYRIDATE); 2-chloro-4,6-bis-(ethylamino)-1,3,5-triazine (SIMAZINE); 2,4-bis-[N-ethylamino]-6-methylthio-1,3,5-triazine (SIMETRYNE); 4-ethylamino-2-t-butylamino-6-methylthio-s-triazine (TERBUTRYNE); methyl 3-[[[[(4-methoxy-6-methyl-1,3,5-triazin-2-yl)-amino]-carbonyl]-amino]-sulphonyl]-thiophene-2-carboxylate (THIAMETURON); S-(2,3,3-trichloroallyl) N,N-diisopropylthiocarbamate (TRIALLATE) and 2,6-dinitro-4-trifluoromethyl-N,N-dipropylaniline (TRIFLURALIN). Some mixtures surprisingly also show synergistic action.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 5 g and 5 kg per ha.

The preparation and use of the active compounds according to the invention can be seen from the following examples.

PREPARATION EXAMPLES

EXAMPLE 1

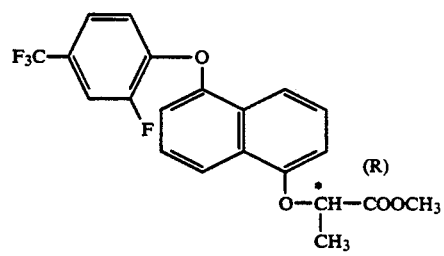

(Process (a))

A mixture of 1.3 g (4 mmol of 5-(2-fluoro-4-trifluoromethyl-phenoxy)-1-naphthol, 0.5 g (4 mmol) of methyl (S)-α-chloropropionate, 0.6 g (4.4 mmol) of potassium carbonate and 50 ml of acetonitrile is stirred for 3 days at 20° C. and for 6 hours under reflux, the mixture is then concentrated, the concentrate is shaken with water/methyl tert-butyl ether, and the organic phase is separated off, dried with sodium sulphate and filtered. The solvent is carefully distilled off from the filtrate under a water pump vacuum.

1.2 g (73.5% of theory) of methyl (R)-α-(5-(2-fluoro-4-(trifluoromethyl-phenoxy)-naphthalen-1-yl-oxy) -propionate are obtained as an amorphous residue. $^1$H-NMR (CDCl$_3$, δ): 4.98 ppm (q)

EXAMPLE 2

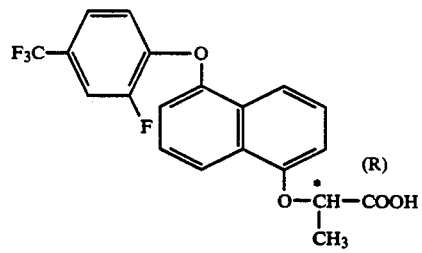

(Process (c))

A mixture of 15.8 g(39 mmol) of methyl (R)-α-(5-(2-fluoro-4-trifluoromethyl-phenoxy)-naphthalen-1-yl -oxy)-propionate, 2.0 g (49 mmol) of sodium hydroxide and 150 ml of water is refluxed for 15 hours, cooled, acidified with 2N hydrochloric acid, and stirred for 30 minutes at about 10° C. The product which has been obtained is crystalline form is isolated by filtration with suction.

14.6 g (95% of theory) of (R)-α-(5-(2-fluoro-4-trifluoromethyl-phenoxy)-naphthalen-1-yl-oxy)propionic acid of melting point 166° C. are obtained.

EXAMPLE 3

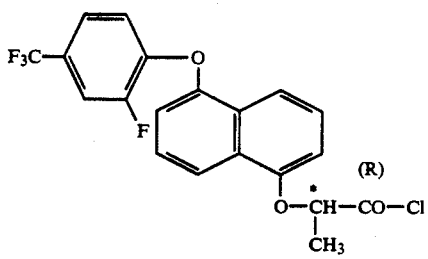

(Process (d))

A mixture of 1.3 g (3.3 mmol) of (R)-α-(5-(2-fluoro-4-trifluoromethyl-phenoxy)-naphthalen-1-yl-oxy) -propionic acid and 20 ml of thionyl chloride is refluxed for 15 hours. Excess thionyl chloride is subsequently carefully removed by distillation under a steam-jet vacuum (about 5 mbar).

(R)-α-(5-(2-Fluoro-4-trifluoromethyl-phenoxy)-naphthalen-1-yl-oxy)-propionyl chloride is obtained as an amorphous residue. The product is employed for further reactions without further purification (cf. Example 4).

EXAMPLE 4

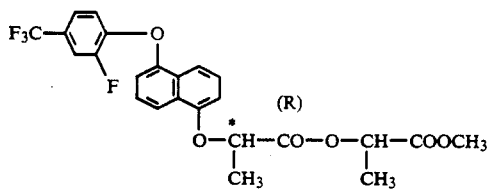

(Process (e))

A mixture of 1.4 g (3.3 mmol) of (R)-α-(5-(2-fluoro-4-trifluoromethyl-phenoxy)-naphthalen-1-yl-oxy) -propionyl chloride, 0.4 g (3.5 mmol) of methyl lactate, 0.5 g (5 mmol) of triethylamine and 50 ml of methylene chloride is stirred for 15 hours at 20° C. and subsequently concentrated.

The residue is shaken with water/methyl tert-butyl ether, and the organic phase is separated off, washed in succession with 2N hydrochloric acid and with 5% strength sodium hydrogen carbonate solution, dried with sodium sulphate and filtered. The solvent is distilled off from the filtrate, and the residue is purified by column chromatography (toluene/silica gel).

1.1 g (69% of theory) of 1-methoxycarbonyl-ethyl (R)-α-(5-(2-fluoro-4-trifluoromethyl-phenoxy)-naphthalen-1-yl-oxy)-propionate are obtained as an amorphous mass. $^1$H-NMR (CDCl$_3$, δ): 5.5 ppm (q)

EXAMPLE 5

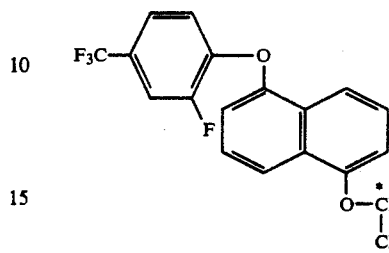

(Process (f))

A mixture of 3.9 g (10 mmol) of (R)-α-(5-(2-fluoro-4-trifluoromethyl-phenoxy)-naphthalen-1-yl-oxy) -propionic acid, 0.2 ml of concentrated sulphuric acid and 200 ml of isopropanol is refluxed for 15 hours, subsequently concentrated, stirred with 5% strength sodium hydrogen carbonate solution, and shaken with methyl tertbutyl ether. The organic phase is separated off, dried with sodium sulphate and filtered. The solvent is carefully distilled off from the filtrate under a water pump vacuum.

3.5 g (80% of theory) of isopropyl (R)-α-(5-(2-fluoro-4-trifluoromethyl-phenoxy)-naphthalen-1-yl-oxy) -propionate are obtained as an amorphous residue. $^1$H-NMR (CDCl$_3$, δ): 4.92 ppm (q)

The compounds of the formula (I) listed in Table 1 can, for example, also be prepared analogously to Examples 1 to 5 and following the general description of the preparation processes according to the invention.

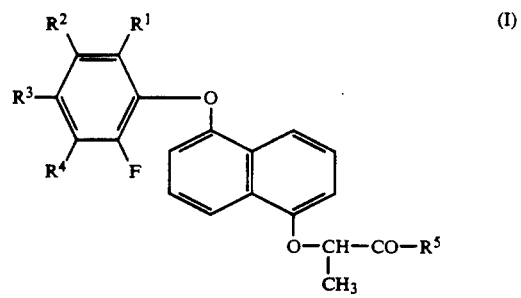

TABLE 1

| Examples of the compounds of the formula (I) | | | | | |
|---|---|---|---|---|---|
| Example No. | R$^1$ | R$^2$ | R$^3$ | R$^4$ | R$^5$ | Physical data |
| 6 | H | H | CF$_3$ | H | OC$_4$H$_9$-n | δ = 4.97 ppm |
| 7 | H | H | CF$_3$ | H | OC$_2$H$_5$ | δ = 4.95 ppm |
| 8 | H | H | CF$_3$ | H | N(OCH$_3$)(CH$_3$) | m.p.: 117° C. |
| 9 | H | H | CF$_3$ | H | 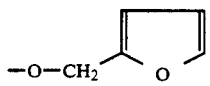 | δ = 5.17 ppm |

TABLE 1-continued

Examples of the compounds of the formula (I)

| Example No. | R¹ | R² | R³ | R⁴ | R⁵ | Physical data |
|---|---|---|---|---|---|---|
| 10 | H | H | $CF_3$ | H | -N(-O-CH₂CH₂CH₂-) (pyrrolidinyl-N-oxy) | (amorphous) |
| 11 | H | H | $CF_3$ | H | $-O-(CH_2)_3-O-CH_2-C_6H_5$ | (amorphous) |
| 12 | H | H | $CF_3$ | H | $-O-(CH_2)_2-O-N=C(CH_3)_2$ | (amorphous) |
| 13 | H | H | $CF_3$ | H | $-O-CH_2-C_6H_5$ | $\delta = 5.00$ ppm |
| 14 | H | H | $CF_3$ | H | $-O-CH_2-C\equiv CH$ | $\delta = 4.78$ ppm |
| 15 | H | H | $CF_3$ | H | $-S-CH_3$ | $\delta = 5.08$ ppm |

STARTING SUBSTANCES OF THE FORMULA (II)

EXAMPLE (II-1)

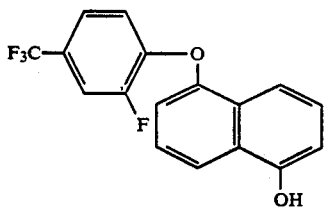

3.4 g (0.06 mol) of potassium hydroxide (powder) are added to a solution of 16.0 g (0.10 mmol) of 1,5-dihydroxynaphthalene in 150 ml of dimethyl sulphoxide, and the mixture is stirred for 60 minutes at 20° C. 6.6 g (0.036 mol) of 3,4-difluoro-benzotrifluoride are then added; the reaction mixture is stirred for 20 hours at 60° C. and then for 50 hours at 80° c. and subsequently concentrated under a steam-jet vacuum. The residue is stirred with 2N hydrochloric acid and the mixture is shaken with ethyl acetate. The organic phase is separated off, dried with sodium sulphate and filtered. The solvent is distilled off from the filtrate under a water pump vacuum, the residue is boiled up in toluene, the mixture is filtered over silica gel, the filter is concentrated, and the residue is triturated with ligroin and filtered off with suction.

2.4 g (21% of theory) of 5-(2-fluoro-4-tri-fluoromethyl-phenoxy)-1-naphthol are obtained as an amorphous product.

USE EXAMPLES

In the use examples which follow, the compound listed below is used as a comparison substance:

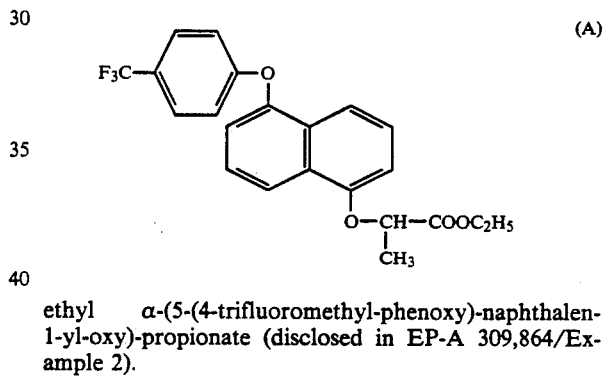

ethyl α-(5-(4-trifluoromethyl-phenoxy)-naphthalen-1-yl-oxy)-propionate (disclosed in EP-A 309,864/Example 2).

EXAMPLE A

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 1,000 l of water/ha. After three weeks, the degree of damage to the plants is rated in % damage in comparison to the development of the untreated control. The figures denote:

0% = no action (like untreated control)

100% = total destruction

In this test, an activity which is up to 90% higher and a superior crop plant selectivity compared with the prior art is shown, for example, by the compound according to Preparation Example 1, 7, 10, 11 and 12.

EXAMPLE B

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient here to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)

100% = total destruction

In this test, an activity which is up to 80% higher compared with the prior art is shown, for example by the compound according to Preparation Example 1.

EXAMPLE C

Water-service treatment under flooded conditions for paddy field weeds (Pot test)

| Preparation of active compounds | |
|---|---|
| Solvent: | 5 parts by weight of acetone |
| Emulsifier: | 1 part by weight of benzyloxy-polyglycol ether |

To produce a suitable preparation of active compound, 1 part by weight of active compound was mixed with the stated amount of solvent, the stated amount of emulsifier was added and the concentrate was diluted with water to the desired concentration.

Test method

Pots (1/5,000 are) were filled with paddy field soil. Two rice plants (variety: Kinmaze) per pot at the 2- or 3-leaves stage (about 10 cm high) were transplanted. Echinochloa crus-galli, Monochoria and/or Eleocharis acicularis L. were inoculated and maintained in wet condition. Two days after transplantation, each pot was placed in flooded condition to a depth of 3 cm.

The dosage of the active compound were applied by watering the preparation of the active compound. After treatment, water in pots was being leached for two days at a rate of 2 to 3 cm per day. After this leaching, each pot was maintained in flooded condition to a depth of 3 cm. Four weeks after treatment with chemicals, the degree of damage to the plants is rated in % damages in comparison to the development of the untreated control. The figures denote 0% = no action (like untreated control)

100% = total destruction.

In this test, an activity up to 100% against weeds is shown, for example, by the compounds according to Examples 7, 10, 11 and 12.

What is claimed is:

1. A fluorine-substituted α-(5-aryloxy-naphthalen-1-yl-oxy)-propionic acid derivative of the formula

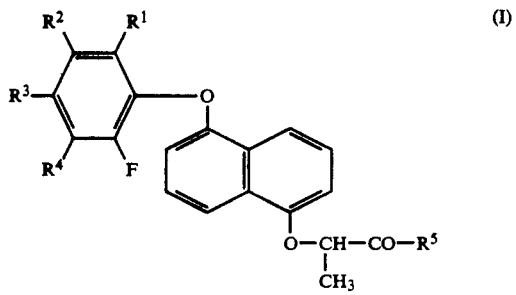

in which
R$^1$ represents hydrogen,
R$^2$ represents hydrogen, fluorine or chlorine,
R$^3$ represents fluorine, chlorine, cyano, trifluoromethyl or trifluoromethylsulphonyl,
R$^4$ represents hydrogen, fluorine or chlorine and
R$^5$ represents chlorine, hydroxyl, amino, C$_1$–C$_6$-alkylamino, C$_3$–C$_4$-alkenylamino, C$_3$–C$_4$-alkinylamino, phenylamino, benzylamino, C$_1$–C$_4$-alkoxycarbonyl-C$_1$–C$_2$-alkylamino, cyanoamino, di-(C$_1$–C$_4$-alkyl)-amino, di-(C$_3$–C$_4$-alkenyl)-amino, C$_1$–C$_4$-alkylsulphonylamino, phenylsulphonylamino, tolylsulphonylamino, hydroxylamino, C$_1$–C$_6$-alkoxyamino, N-(C$_1$–C$_6$-alkoxy)-N-(C$_1$–C$_4$-alkyl)amino, hydrazino, C$_1$–C$_4$-alkylsulphonylhydrazino, phenylsulphonylhydrazino, tolylsulphonylhydrazino, C$_1$–C$_4$-alkylthio, phenylthio, benzylthio, C$_1$–C$_4$-alkoxy-carbonyl-C$_1$–C$_2$-alkylthio or the group —O—R$^6$ where
R$^6$ represents a radical selected from the group consisting of C$_1$–C$_6$-alkyl, C$_3$–C$_4$-alkenyl, C$_3$–C$_4$-alkinyl, C$_1$–C$_4$-alkoxy-C$_1$–C$_4$-alkyl, C$_1$–C$_4$-alkylthio-C$_1$–C$_4$-alkyl, C$_1$–C$_4$-alkylsulphinyl-C$_1$–C$_4$-alkyl, C$_1$–C$_4$-alkylsulphonyl-C$_1$–C$_4$-alkyl, phenoxy-C$_1$–C$_3$-alkyl, trimethylsilylmethyl, phenylthio-C$_1$–C$_3$-alkyl, benzyloxy-C$_1$–C$_3$-alkyl, benzylthio-C$_1$–C$_3$-alkyl, C$_1$–C$_4$-alkoxy-carbonyl-C$_1$–C$_2$-alkyl, C$_1$–C$_4$-alkylamino-carbonyl-C$_1$–C$_2$-alkyl, benzyl, pyrazolyl-C$_1$–C$_4$-alkyl, C$_2$–C$_4$-alkylideneaminooxy-C$_1$–C$_4$-alkyl and C$_2$–C$_4$-alkylideneamino, each of which is optionally substituted by fluorine and/or chlorine, or represents an ammonium, a C$_1$–C$_4$-alkylammonium, a sodium, potassium or calcium equivalent, or represents the group

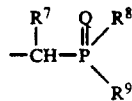

where
R$^1$ represents hydrogen, C$_1$–C$_4$-alkyl, phenyl, furyl, thienyl or pyridyl, $R^8$ represents $C_1$–$C_4$-alkyl or $C_1$–$C_4$-alkoxy,
$R^9$ represents $C_1$–$C_4$-alkoxy and
Q represents oxygen or sulphur, or
$R^6$ represents the group —$(CH_2)_n$—$R^{10}$ where
n represents the numbers 0, 1 or 2 and
$R^{10}$ represents a heterocyclic radical selected from the group consisting of furyl, tetrahydrofuryl, oxotetrahydrofuryl, thienyl, tetrahydrothienyl, perhydropyranyl, oxazolyl, thiazolyl, thiadiazolyl, dioxolanyl, perhydropyrrolyl, oxoperhydropyrrolyl, isoxazolidinyl, pyridinyl or pyrimidinyl, each of which is optionally substituted by fluorine, chlorine, bromine and/or $C_1$–$C_4$-alkyl.

2. A compound of the formula (I) according to claim 1, in which
$R^1$ represents hydrogen,
$R^2$ represents hydrogen or fluorine,
$R^3$ represents trifluoromethyl or trifluoromethylsulphonyl,
$R^4$ represents hydrogen or fluorine, and
$R^5$ represents chlorine, hydroxyl, amino, $C_1$–$C_4$-alkylamino, phenylamino, $C_1$–$C_4$-alkoxy-carbonyl-$C_1$–$C_2$-alkylamino, di-($C_1$–$C_3$-alkyl)-amino, $C_1$–$C_4$-alkylsulphonylamino, phenylsulphonylamino, hydroxyamino, cyanoamino, $C_1$–$C_4$-alkoxyamino, N-($C_1$–$C_4$-alkoxy)-N-($C_1$–$C_3$-alkyl)-amino, hydrazino, $C_1$–$C_4$-alkylsulphonylhydrazino, phenylsulphonylhydrazino, $C_1$–$C_4$-alkylthio or $C_1$–$C_4$-alkoxy-carbonyl-$C_1$–$C_2$-alkylthio, or represents the group —O—$R^6$ where
$R^6$ represents $C_1$–$C_4$-alkyl, $C_1$–$C_2$-alkoxy-$C_1$–$C_2$-alkyl, $C_1$–$C_2$-alkylthio-$C_1$–$C_2$-alkyl, $C_1$–$C_2$-alkylsulphinyl-$C_1$–$C_2$-alkyl, $C_1$–$C_2$-alkylsulphonyl-$C_1$–$C_2$-alkyl, benzyloxy-$C_1$–$C_3$-alkyl, benzylthio-$C_1$–$C_3$-alkyl, $C_1$–$C_4$-alkoxycarbonyl-$C_1$–$C_2$-alkyl, $C_1$–$C_4$-alkylaminocarbonyl-$C_1$–$C_2$-alkyl, benzyl, trimethylsilylmethyl, $C_2$–$C_4$-alkylideneaminooxy-$C_2$–$C_3$-alkyl or represents an ammonium, $C_1$–$C_3$-alkylammonium, sodium, or potassium equivalent, or represents the group

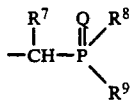

where
$R^7$ represents hydrogen, methyl, phenyl, furyl, thienyl or pyridyl,
$R^8$ represents methoxy or ethoxy,
$R^9$ represents methoxy or ethoxy,
Q represents oxygen or sulphur,
or
$R^6$ represents the group (—$CH_2$—)$_n$—$R^{10}$ where
n represents the numbers 0, 1 or 2 and
$R^{10}$ represents a heterocyclic radical selected from the group consisting of furyl, tetrahydrofuryl, thienyl, perhydropyranyl, oxazolyl, thiazolyl, isoxazolidinyl and dioxolanyl, each of which is optionally substituted by chlorine and/or methyl.

3. A compound of the formula (I) according to claim 1, in which
$R^1$, $R^2$ and $R^4$ represent hydrogen,
$R^3$ represents trifluoromethyl and
$R^5$ represents chlorine, hydroxyl, methoxy, ethoxy, propoxy, isopropoxy, n-butoxy, isobutoxy, sec-butoxy, t-butoxy, methoxyethoxy, ethoxyethoxy, benzyloxyethoxy, benzyloxypropoxy, methoxycarbonylmethoxy, ethoxycarbonylmethoxy, methoxycarbonylethoxy, ethoxycarbonylethoxy or isopropylindenaminooxyethoxy.

4. A herbicidal composition comprising a herbicidally effective amount of a fluorine-substituted α-(5-aryloxynaphthalen-1-yl-oxy)-propionic acid derivative of the formula (I) according to claim 1 and an extender.

5. A method of combating unwanted vegetation, which comprises applying to the vegetation or to a locus from which it is desired to exclude such vegetation a herbicidally effective amount of a fluorine-substituted α-(5-aryloxy-naphthalen-1-yl-oxy)-propionic acid derivative of the formula (I) according to claim 1.

* * * * *